United States Patent
Clark et al.

(10) Patent No.: US 6,939,962 B2
(45) Date of Patent: Sep. 6, 2005

(54) METHOD FOR THE SYNTHESIS OF SUCROSE-6-ESTERS

(75) Inventors: Jason D. Clark, Fort Collins, CO (US); Richard R. LeMay, Jr., Howell, NJ (US)

(73) Assignee: Tate & Lyle Public Limited Company, London (GB)

( * ) Notice: Subject to any disclaimer, the term of this patent is extended or adjusted under 35 U.S.C. 154(b) by 31 days.

(21) Appl. No.: 10/343,378

(22) PCT Filed: Jul. 19, 2001

(86) PCT No.: PCT/GB01/03245
§ 371 (c)(1),
(2), (4) Date: Jan. 31, 2003

(87) PCT Pub. No.: WO02/10180
PCT Pub. Date: Feb. 7, 2002

(65) Prior Publication Data
US 2003/0158404 A1 Aug. 21, 2003

(30) Foreign Application Priority Data
Jul. 31, 2000 (GB) .............................................. 0018784

(51) Int. Cl.$^7$ .......................... C07H 1/00; C07H 13/06; C07H 15/04
(52) U.S. Cl. ....................... 536/124; 536/115; 536/116; 536/119; 536/120
(58) Field of Search ................................ 536/124, 115, 536/116, 119, 120

(56) References Cited
U.S. PATENT DOCUMENTS
5,470,969 A * 11/1995 Sankey et al. .............. 536/115

FOREIGN PATENT DOCUMENTS
EP 475619 A1 * 3/1992

* cited by examiner

Primary Examiner—James O. Wilson
Assistant Examiner—Everett White
(74) Attorney, Agent, or Firm—Dickstein, Shapiro, Morin & Oshinsky, LLP.

(57) ABSTRACT

There is described a process for the synthesis of a sucrose-6-ester comprising: (a) reacting a mixture comprising sucrose and a polar aprotic solvent with an organotin-based acylation promoter, while adding a solvent capable of removing water by co-distillation, and removing water by co-distillation, to afford a first reaction mixture which is substantially free from water, followed by (b) adding a carboxylic anhydride to said first reaction mixture to afford a second reaction mixture, and maintaining said second reaction mixture at a temperature and for a period of time sufficient to produce a sucrose-6-ester, characterised in that step (a) is performed at a temperature of from 85 to 125° C. and at a pressure of from 20 to 80 kPa. In the most preferred embodiment, the polar aprotic solvent is DMF, the solvent capable of removing water by co-distillation is cyclohexane, the organotion-based acylation promoter is a 1,3-diacyloxy-1,1,3,3-tetrabutyldistannoxane, and step (a) is performed at approximately 97° C., and approximately 50 kpa, until the weight ratio of tin to water in the first reaction mixture is greater than about 26, when the tin content is measured by X-Ray Fluoresence Analyzer, and the water content is measured by the Karl-Fischer method.

20 Claims, No Drawings

METHOD FOR THE SYNTHESIS OF SUCROSE-6-ESTERS

This invention relates to an improved method for the synthesis of sucrose-6-esters.

Sucrose-6-esters are important intermediates in the synthesis of the artificial sweetener sucralose (4,1',6'-trichloro-4,1',6'-trideoxygalactosucrose).

A number of tin-mediated routes for the preparation of sucrose-6-esters have been disclosed, for example in U.S. Pat. No. 4,950,746, U.S. Pat. No. 5,023,329, and U.S. Pat. No. 5,089,690. Each of these documents discloses a different organotin-based acylation promoter: U.S. Pat. No. 4,950,746 employs a 1,3-di(hydrocarbyloxy)-1,1,3,3-tetra-(hydrocarbyl)distannoxane reagent; U.S. Pat. No. 5,023,329 employs a di(hydrocarbyl)tin oxide; and U.S. Pat. No. 5,089,608 employs the reaction product of a di(hydrocarbyl)tin oxide and a dihydric alcohol, an alkanolamine, or an enolizable α-hydroxyketone.

More particularly, EP-0 475 619-A discloses a process for producing a sucrose-6-ester, which comprises reacting sucrose with a carboxylic anhydride in a reaction mixture comprising a polar aprotic solvent and a 1,3-diacyloxy-1,1,3,3-tetra-(hydrocarbyl)distannoxane for a period of time sufficient to produce a sucrose-6-ester. In EP-0 475 619-A there is also disclosed a process for producing a sucrose-6-ester comprising slurrying sucrose and a 1,3-diacyloxy-1,1,3,3-tetra-(hydrocarbyl)distannoxane in a reaction mixture comprising a mixed solvent system containing a polar aprotic solvent and a hydrocarbon-like co-solvent capable of removing any water present in the reaction mixture by codistillation, and then, after removal of the water, treating the reaction mixture with a carboxylic acid anhydride.

An improvement in this method is disclosed in EP-0 776 903-A. That improvement comprises passing vapours of a solvent capable of removing water by codistillation (codistillation solvent) through a reaction mixture containing a polar aprotic solvent, sucrose, and a 1,3-diacyloxy-1,1,3,3-tetra-(hydrocarbyl)distannoxane, in sufficient quantity and sufficient time to remove substantially all the of the water in said reaction mixture by co-distillation.

According to the present invention, there is provided a process for the synthesis of a sucrose-6-ester comprising:

(a) reacting a mixture comprising sucrose and a polar aprotic solvent with an organotin-based acylation promoter, while, substantially continuously, adding a solvent capable of removing water by co-distillation, and removing water by co-distillation, to afford a first reaction mixture which is substantially free from water, followed by (b) adding a carboxylic anhydride to said first reaction mixture to afford a second reaction mixture, and maintaining said second reaction mixture at a temperature and for a period of time sufficient to produce a sucrose-6-ester, characterised in that step (a) is performed at a temperature of from 85 to 125° C. and at a pressure of from 20 to 80 KPa.

The polar aprotic solvent is preferably N,N-dimethylformamide (DMF). Other suitable solvents are N-methyl-2-pyrrolidone, dimethyl sulfoxide, N,N-dimethylacetamide, and hexamethylphosphoramide. The choice is determined by the solubility of the sucrose and the 1,3-diacyloxy-1,1,3,3-tetra-(hydrocarbyl)distannoxane or other organotin-based acylation promoter (and the stannylated sucrose product) in the solvent, as well as by safety and toxicity considerations, especially if the sucrose-6-ester is to be used for the synthesis of sucralose, a food additive.

The amount of the polar aprotic solvent to be used will also be determined by the above-mentioned solubility considerations. When the polar aprotic solvent is DMF, it is preferably used in an amount of from 4 to 10 g/g sucrose, and more preferably from 4.5 to 5.5 g/g sucrose.

Many solvents are capable of removing water by co-distillation, and any solvent that can achieve this can be used in the method of the present invention. Preferred solvents are those which are immiscible with water and form a constant-composition minimum-boiling azeotrope with water. Exemplary classes of solvents are saturated hydrocarbons, aromatic hydrocarbons, chlorinated hydrocarbons, ketones, and ethers. As for the polar aprotic solvent, safety and toxicity considerations will also affect the choice of an appropriate solvent. Hydrocarbons are preferred, and cyclohexane, n-heptane, toluene, and isooctane (2,2,4-trimethylpentane) are particularly preferred The most preferred solvent is cyclohexane.

The codistillation solvent is added to the mixture during step (a) substantially continuously, and is conveniently also added at a substantially constant rate. However, changes in the rate of addition during step (a), and even stopping the addition altogether for a portion of the reaction, are also possible.

The prior art EP-0 776 903-A prescribes that the solvent capable of removing water by codistillation be added in gaseous form. That is, the solvent, typically cyclohexane, is preheated, and vapours of the solvent added to the reaction mixture. While this procedure can be used in the method of the present invention, it has been found that it is also possible to add the solvent directly as a liquid, without pre-heating. Typically, the solvent will be added through a polytetrafluoroethylene (PTFE) tube, into the mixture, preferably close to the agitator of the reaction vessel. It will be appreciated that, under these conditions, the solvent will then vaporise rapidly.

It is preferred to recover and re-use the codistillation solvent. This can easily be achieved by condensing the vapours from the reaction vessel, and then washing and drying the condensate. More preferably, the codistillation solvent is recycled during the reaction. This can be achieved by condensing the codistillation solvent into a reservoir during the reaction, and using that reservoir as the supply for the codistillation solvent to be added to the reaction mixture. In the case that the polar aprotic solvent is DMF and the codistillation solvent is cyclohexane, it has been found that it is best to add a small amount of water to the reservoir. This is because a small amount of DMF co-distills from the reaction vessel with the water and the cyclohexane. The DMF can dissolve in the cyclohexane in the reservoir, and thereby solubilise water in the cyclohexane. When water is already present in the reservoir, most of the DMF is taken into the aqueous layer, reducing the solubility of water in the cyclohexane, and thereby affording drier cyclohexane.

The organotin-based acylation promoter can be any of those known in the art per se, for example any of those disclosed in U.S. Pat. No. 4,950,746, U.S. Pat. No. 5,023,329, U.S. Pat. No. 5,089,608, or EP-0 475 619-A. In particular, the organotin-based acylation promoter can be selected from the group consisting of: a 1,3-dihydrocarbyloxy)-1,1,3,3-tetra-(hydrocarbyl)distannoxane; a di(hydrocarbyl)tin oxide; the reaction product of a di(hydrocarbyl)tin oxide and a dihydric alcohol, an alkanolamine, or an enolizable α-hydroxyketone; and a 1,3-diacyloxy-1,1,3,3-tetra-(hydrocarbyl)distannoxane. The organotin-based acylation promoter is preferably a 1,3-diacyloxy-1,1,3,3-tetra-(hydrocarbyl)distannoxane.

By "hydrocarbyl" as used herein, is meant an alkyl, cycloalkyl, aryl, or aralkyl group.

When the organotin-based acylation promoter is a 1,3-di(hydrocarbyloxy)-1,1,3,3-tetra-(hydrocarbyl)distannoxane, the hydrocarbyloxy group is preferably a $C_1$–$C_8$ alkoxy group or phenoxy, more preferably methoxy, ethoxy, n-propyloxy, n-butyloxy, n-pentyloxy or n-hexyloxy, and most preferably a methoxy group. The hydrocarbyl group in turn is preferably an alkyl group, more preferably a $C_1$–$C_8$ alkyl group, and most preferably an n-butyl group.

When the organotin-based acylation promoter is a di(hydrocarbyl)tin oxide, the hydrocarbyl group is preferably an alkyl group, more preferably a $C_1$–$C_8$ alkyl group, and most preferably an n-butyl group.

When the organotin-based acylation promoter is the reaction product of a di(hydrocarbyl)tin oxide and a dihydric alcohol, an alkanolamine, or an enolizable α-hydroxyketone, the di(hydrocarbyl)tin oxide is preferably as described above. The dihydric alcohol can be an alkane diol, preferably having from 2 to 8 carbon atoms. Suitable examples are ethylene glycol, 2,3-propanediol, 2,3-butanediol, 1,3-butanediol, 1,4-butanediol, 1,3-propanediol, 1,2-pentanediol, and 1,2-hexanediol. Alternatively, the dihydric alcohol can be a cycloalkane diol, preferably having from 5 to 8 carbon atoms. Suitable examples are 1,2-cyclohexanediol and 1,2-cyclopentanediol. In both cases, it is preferred that the two hydroxyl groups are not more than four carbon atoms distant from each other on the carbon chain to which they are bonded, and it is more preferred that they be on adjacent carbon atoms or that there be only one carbon atom separating the carbon atoms to which the hydroxyl groups are bonded. The alkanolamine is preferably a $C_2$–$C_8$ alkanolamine, and preferably the hydroxyl group and the amino group are not more than four carbon atoms distant from each other on the carbon chain to which they are bonded, and more preferably the hydroxyl group and the amino group are on adjacent carbon atoms or there is only one carbon atom separating the carbon atoms to which the hydroxyl group and the amino group are bonded. Suitable alkanolamines are ethanolamine, 2-amino-1-propanol, and 1-amino-2-propanol. Suitable enolisable α-hydroxyketones are benzoin (2-hydroxy-2-phenylacetophenone) and acetoin (3-hydroxy-2-butanone).

Preferably, however, the organotin-based acylation promoter is a 1,3-diacyloxy-1,1,3,3-tetra-(hydrocarbyl)distannoxane. The hydrocarbyl group of the 1,3-diacyloxy-1,1,3,3-tetra-(hydrocarbyl)distannoxane is preferably an alkyl group, more preferably a $C_1$–$C_8$ alkyl group, and most preferably a butyl group, so that 1,1,3,3-tetrabutyldistannoxanes are particularly preferred. It is convenient if the acyloxy group matches that of the carboxylic anhydride to be used, so that, for example, when a sucrose-6-acetate is being synthesised, 1,3-diacetoxy-1,1,3,3-tetrabutyldistannoxane (distannoxane diacetate DSDA) is most preferred.

When the organotin-based acylation promoter is a dinuclear species containing two atoms of tin per molecule (e.g. a distannoxane), it is preferably present in from 0.5 to 2.5 molar equivalents (per mole of sucrose), more preferably from 0.75 to 1.2 molar equivalents, still more preferably from 0.9 to 1.1 molar equivalents, and most preferably 1.0 molar equivalents.

When the organotin-based acylation promoter is a mononuclear species containing one atom of tin per molecule (e.g. a di(hydrocarbyl)tin oxide), it is preferably present in from 0.5 to 2.5 molar equivalents (per mole of sucrose), more preferably from 0.8 to 1.5 molar equivalents, and most preferably 1.2 molar equivalents.

When the organotin-based acylation promoter is a 1,3-diacyloxy-1,1,3,3-tetra-(hydrocarbyl)distannoxane, it is preferably recovered after the end of step (b) and reused. This can be achieved by partitioning the product mixture between water and cyclohexane, creating an upper 1,3-diacyloxy-1,1,3,3-tetra-(hydrocarbyl)distannoxane/cyclohexane phase, and a lower sucrose ester/DMF/water/acetic acid phase, and then further extracting the lower phase with cyclohexane. The combined cyclohexane extracts are then combined and concentrated, preferably under reduced pressure. The 1,3-diacyloxy-1,1,3,3-tetra-(hydrocarbyl)distannoxane can be further purified by conventional techniques.

The end-point of the reaction of step (a) can be conveniently determined by the weight ratio of tin to water in the reaction mixture. The tin content can measured using an X-Ray Fluoresence Analyzer, and the water content can be measured by the Karl-Fischer method. It has been found that the weight ratio of tin to water at the end of step (a) should be from 20 to 35, more preferably from 24 to 32, and most preferably from 26 to 28, for optimum yields. Therefore, it is most convenient to monitor the progression of the reaction by measuring the tin to water ratio of aliquots, and allowing step (a) to proceed until the weight ratio is greater than about 26.

Step (a) is preferably performed at a temperature of from 90 to 100° C., more preferably at a temperature of from 93 to 98° C., and most preferably at approximately 97° C. Step (a) is further preferably performed at a pressure of from 33 to 66 kPa, more preferably at a pressure of from 40 to 60 kPa, and most preferably at roughly half atmospheric pressure, namely at a pressure of approximately 50 kPa.

The method of the present invention can be used to prepare a variety of sucrose-6-esters, provided that the appropriate carboxylic anhydride is available. In particular, the method can be used to prepare sucrose-6-acetate, by the use of acetic anhydride, and sucrose-6-benzoate, by the use of benzoic anhydride. As mentioned before, it is convenient, but not necessary, to then use an acyloxytin reagent having the same acyloxy group as the ester to be prepared.

The carboxylic anhydride is preferably added in an amount of from 0.8 to 1.5 molar equivalents (per mole of sucrose starting material), more preferably from 1.05 to 1.35 molar equivalents, still more preferably from 1.1 to 1.25 molar equivalents, and most preferably 1.15 molar equivalents. Too much carboxylic anhydride results in the formation of excessive amounts of dicarboxylate by-products, while too little results in large amounts of sucrose being recovered at the end of the reaction.

In the method of the present invention, it has surprisingly been found that, compared with the prior art method of EP-0 776 903-A, by performing the reaction at essentially the prior art temperature, but with only a moderate reduction of the pressure (typically to approximately half atmospheric pressure), the time taken for the reaction of part (a) to proceed to completion (as measured by the tin/water weight ratio) is greatly reduced. As shown in the Examples, typically the reaction at reduced pressure can be complete in approximately half the time of the reaction at atmospheric pressure. The reduced reaction time is of itself a benefit, but also results in a pro rata reduction in cyclohexane usage.

The quality of the sucrose-6-ester product is also improved compared with that produced by the prior art method of EP-0 776 903-A. Degradation products, which hamper the extraction of the tin reagent at the end of the reaction, and also give the product a dark colour, are reduced by the method of the present invention. Also, surprisingly, the ratio of sucrose-6-ester to (unwanted) sucrose-2-ester is improved.

EXAMPLES

General Experimental Method

A 2 litre 5-necked round bottom flask is equipped with a mechanical stirrer, a septum seal, a thermocouple connected to a solvent recycle pump, a Vigreux distillation column, and, via a Y-shaped glass adapter, a 6 mm polytetrafluoroethylene (PTFE) tube for cyclohexane inlet (connected via the solvent recycle pump to the solvent reservoir), and a pressure equilibrated dropping funnel. The Vigreux column is connected via a water-cooled condenser ending with an adapter with vacuum take-off to the solvent reservoir, which is a 2-litre round bottom flask, to which the PTFE cyclohexane inlet tube leads via the solvent recycle pump.

The reaction vessel is charged with 140.3 g (0.41 mol) of sucrose and 700 ml of dimethylformamide (DMF). The pressure-equilibrated dropping funnel is charged with a solution of DSDA in cyclohexane (0.41 mol, 1 eq). The solvent reservoir is charged with 1 litre of dry cyclohexane and 50 ml of water.

The temperature controller is set to 97° C., and the reaction flask is heated using a heating mantle, with moderate stirring. Once the sucrose has dissolved in the DMF, (internal temperature approximately 85° C.), the required vacuum is applied.

Once the temperature of the reaction mixture reaches 100° C., the DSDA solution is slowly added, at such a rate as to keep the temperature above 93° C.

Once the DSDA addition is complete, the cyclohexane recycle pump is turned on, being controlled by the temperature controller so as to be activated when the temperature of the reaction mixture is 97° C. or above. A cyclohexane/water mixture, together with some DMF, distills through the Vigreux column and condenses into the solvent reservoir, from which the cyclohexane is supplied to the reaction mixture.

Samples are removed periodically by syringe through the septum cap, and analysed for tin content and water content. Tin content is determined using an X-ray fluorescence analyser (XRF) from ASOMA, while water is determined using a Karl-Fischer moisture titration. Once the tin/water ratio by weight reaches approximately 27, the reaction is stopped, the reactor is equipped with a calcium bicarbonate (DryRite) drying tube (to prevent the inlet of moisture upon cooling), and cooled to 3° C. The DSDA dropping funnel is replaced with a pressure-equalised dropping funnel charged with 1.15 molar equivalents of acetic anhydride. (Correction for the amount of the samples removed for analysis is made). The acetic anhydride is added drop-wise over approximately 20 minutes, ensuring that the temperature of the reaction mixture does not exceed 5° C. The reaction mixture is maintained at this temperature for six hours, and samples are removed at intervals in order to analyse the product distribution.

The mixture is then quenched with approximately 0.6 equivalents of water, and 1 litre cyclohexane. The mixture is stirred for 1 hour, and allowed to warm to room temperature, for complete quenching of the reaction. The layers are separated using a separating funnel (allowing at least 30 minutes for separation to occur), and then the aqueous phase is extracted with 4×1 litre cyclohexane. The cyclohexane extracts are combined and concentrated for recovery of DSDA.

The composition of the product, in order to determine the yield and the distribution of products, is determined by HPLC and GC.

Examples 1 to 8

Using the method set out above, a number of experiments were conducted at atmospheric pressure (Examples 1 to 3, which are comparative Examples), and a range of reduced pressures (Examples 4 to 8, which are Examples according to the invention). The results are given in Table 1.

Preparation of Sucrose-6-Acetate: Vacuum v. Atmospheric Dehydrations

|  | ATMOSPHERIC (comparative Examples) | | | | VACUUM (Examples according to the Invention) | | | | | |
| --- | --- | --- | --- | --- | --- | --- | --- | --- | --- | --- |
| Pressure (kPa) inside reaction vessel | 100 | 100 | 100 | 100 | 50 | 50 | 50 | 50 | 66 | 33 |
| Example Number | 1 | 2 | 3 | Average | 4 | 5 | 6 | Average | 7 | 8 |
| Dehydration Final Tin/Water Ratio | 25.3 | 27.2 | 31.0 | | 28.5 | 29.3 | 26.7 | | 27.5 | 32.7 |
| Total Dehydration Time (min:sec) | 72:00 | 76:00 | 74:00 | | 36:00 | 39:20 | 34:47 | | 31:30 | 18:57 |
| Final Product Wt. (g) | 722.1 | 721.0 | 749.4 | | 603.5 | 588.6 | 623.2 | | 666.3 | 644.9 |
| Assay (Weight %) S-6-A + S-2-A | 17.2 | 16.3 | 16.0 | | 20.4 | 20.8 | 19.5 | | 19.8 | 21.3 |
| Monoacetates | 0.1 | 0.1 | 0.2 | | 0.1 | 0.1 | 0.1 | | 0.1 | 0.1 |
| Diacetates | 2.0 | 1.5 | 1.6 | | 2.0 | 2.0 | 1.7 | | 2.1 | 2.2 |
| Sucrose | 0.8 | 1.8 | 1.3 | | 1.9 | 1.6 | 2.0 | | 0.9 | 0.6 |
| Ratio of S-6-A to S-2-A | 23.5 | 21.2 | 22.9 | 22.2 | 24.1 | 26.3 | 23.9 | 24.8 | 22.4 | 27.8 |
| Carbohydrate S-6-A | 81.9% | 78.7% | 80.6% | | 80.0% | 81.7% | 80.2% | | 82.5% | 84.9% |
| Profile (Weight %) S-2-A | 3.5% | 3.7% | 3.5% | | 3.3% | 3.1% | 3.4% | | 3.7% | 3.1% |
| Monoacetates | 0.7% | 0.7% | 0.8% | | 0.6% | 0.6% | 0.6% | | 0.5% | 0.5% |
| Diacetates | 10.0% | 7.5% | 8.2% | | 8.2% | 8.2% | 7.4% | | 9.3% | 8.9% |
| Sucrose | 4.0% | 9.3% | 6.9% | | 7.9% | 6.5% | 8.4% | | 4.0% | 2.6% |
| Yield: (Corrected) | 81.6% | 77.5% | 79.5% | 79.5% | 80.7% | 80.7% | 78.9% | 80.1% | 86.6% | 89.8% |

The colour of the product of the reaction was quantified by measuring the absorbance in a 1 cm cell at 600 nm against a DMF standard. The results are given in Table 2.

TABLE 2

|  | Comparative Example | Examples according to the Invention | | |
| --- | --- | --- | --- | --- |
| Pressure (kPa) | 100 | 50 | 66 | 33 |
| Absorbance | 1.16 | 0.37 | 0.35 | 0.18 |

The colour measurements for 66 kPa and 33 kPa correspond to the products from Examples 7 and 8, respectively. The colour measurements for 100 kPa and 50 kPa correspond to the averages for the products from comparative Examples 1, 2 and 3, and Examples 4, 5 and 6, respectively.

Thus, it can be seen that the reduced pressure reactions afford a much less intensely coloured product compared with those run at atmospheric pressure, and that the reduction in product colour roughly correlates with the reduction pressure.

What is claimed is:

1. A process for the synthesis of a sucrose-6-ester comprising:
    (a) reacting a mixture comprising sucrose and a polar aprotic solvent with an organotin-based acylation promoter, while, substantially continuously, adding a solvent capable of removing water by co-distillation, and removing water by co-distillation, to afford a first reaction mixture which is substantially free from water, followed by
    (b) adding a carboxylic anhydride to said first reaction mixture to afford a second reaction mixture, and manufacturing said second reaction mixture at a temperature and for a period of time sufficient to produce a sucrose-6-ester, characterized in that step (a) is performed at a temperature of from 85 to 125° C. and at a pressure of from 20 to 80 kPa.

2. A process according to claim 1 wherein said polar aprotic solvent is dimethylformamide.

3. A process according to claim 2 wherein said solvent capable of removing water by co-distillation is cyclohexane.

4. A process according to claim 3, wherein said organotin-based acylation promoter is a 1,3-diacyloxy-1,1,3,3-tetra-(hydrocarbyl)distannoxane.

5. A process according to claim 4, wherein said 1,3-diacyloxy-1,1,3,3-tetra-(hydrocarbyl)distannoxane is 1,3-diacyloxy-1,1,3,3-tetrabutyldistannoxane.

6. A process according to claim 5, wherein, at the end of step (a), the weight ratio of tin to water in the first reaction mixture is from 26 to 28, when the tin content is measured by X-Ray Fluoresence Analyzer, and the water content is measured by the Karl-Fischer method.

7. A process according to claim 6, wherein step (a) is performed at a temperature of approximately 97° C.

8. A process according to claim 7, wherein step (a) is performed at a pressure of approximately 50 kPa.

9. A process according to claim 8, wherein said sucrose-6-ester is a sucrose-6-acetate, and said carboxylic anhydride is acetic anhydride.

10. A process according to claim 9, wherein the solvent capable of removing water by codistillation is recovered and re-used.

11. A process according to claim 9, wherein the solvent capable of removing water by codistillation is recycled during the reaction.

12. A process according to claim 4, wherein the 1,3-diacyloxy-1,1,3,3-tetra-(hydrocarbyl)distannoxane is recovered and re-used.

13. A process according to claim 2 wherein the said aprotic solvent is dimethylformamide in an amount of 4 to 10 g/g sucrose and the organotin-based acylation promoter is a di($C_1$–$C_8$ alkyl)tin oxide in an amount of 0.5 to 5 molar equivalents per mole of sucrose.

14. A process according to claim 13, wherein the dimethylformamide amount is 4.5 to 5.5 g/g sucrose and the organotin-based acylation promoter is a 1,3-diacyloxy-1,1,3,3-tetra-($C_1$–$C_8$ alkyl)distannoxane)tin oxide in an amount of 0.75 to 1.2 molar equivalents per mole of sucrose.

15. A process according to claim 14, wherein the carboxylic anhydride is acetic anhydrive and the organotin-based acylation promoter is a 1,3-diacyloxy-1,1,3,3-tetra-(n-butly)distannoxane)tin oxide in an amount of 0.9 to 1.1 molar equivalents per mole of sucrose.

16. A process according to claim 15, wherein step (a) is performed at a pressure of approximately 50 kPa.

17. A process according to claim 1 wherein said solvent capable of removing water by co-distillation is cyclohexane.

18. A process according to claim 17, wherein said organotin-based acylation promoter is a 1,3-diacyloxy-1,1,3,3-tetra-(hydrocarbyl)distannoxane.

19. A process according to claim 1, wherein step (a) is performed at a pressure of approximately 50 kPa.

20. In a process for the synthesis of sucralose from sucrose via a sucrose-6-ester as an intermediate, the improvement characterized in that the sucrose-6-ester is prepared by a process according to claim 1.

* * * * *